(12) United States Patent
Sexton

(10) Patent No.: US 6,626,818 B2
(45) Date of Patent: Sep. 30, 2003

(54) MAGNETIC THERAPY DEVICE

(76) Inventor: Eugene Sexton, 7800 Nottely Dam Rd., Blairsville, GA (US) 30512

( * ) Notice: Subject to any disclaimer, the term of this patent is extended or adjusted under 35 U.S.C. 154(b) by 53 days.

(21) Appl. No.: 10/083,164

(22) Filed: Feb. 28, 2002

(65) Prior Publication Data

US 2003/0163018 A1 Aug. 28, 2003

(51) Int. Cl.[7] .............................. A61B 17/52; A61N 2/00
(52) U.S. Cl. ............................................................. 600/9
(58) Field of Search .................................. 600/9–15

(56) References Cited

U.S. PATENT DOCUMENTS

| | | | |
|---|---|---|---|
| 4,537,181 A | * | 8/1985 | Shalhoob et al. .............. 600/9 |
| 4,727,857 A | * | 3/1988 | Horl ............................ 600/15 |
| 5,529,568 A | | 6/1996 | Rayman |
| 5,632,720 A | * | 5/1997 | Kleitz ........................... 601/15 |
| 5,667,469 A | * | 9/1997 | Zhang et al. ................... 600/9 |
| 6,065,210 A | * | 5/2000 | Bove ........................ 29/895.21 |
| 6,102,875 A | | 8/2000 | Jones |
| 6,123,657 A | * | 9/2000 | Ishikawa et al. ............... 600/9 |
| 6,231,497 B1 | * | 5/2001 | Souder ........................... 600/9 |

* cited by examiner

*Primary Examiner*—Samuel G. Gilbert
(74) *Attorney, Agent, or Firm*—Harpman & Harpman

(57) ABSTRACT

A magnetic therapy device that affects a compression of multiple magnetic fields by rapid rotation of aligned permanent magnets in relation to a corresponding fixed multiple magnetic fields. A multiplicity of polar magnets are supported in a polar aligned relationship and are rapidly rotated on their longitudinal axis. An opposing multiple magnetic polar field is established and positioned in spaced relation to the rotating magnetic field imparting a therapeutic compression effect of magnetic fields on a biological entity positioned within the fields.

8 Claims, 5 Drawing Sheets

MAGNETIC THERAPY DEVICE

BACKGROUND OF THE INVENTION

1. Technical Field

This device relates to magnetic therapeutic apparatus' that use magnetism to impart physical influences to the human body.

2. Description of Prior Art

Prior art devices of this type have been developed based on modern selective research that has shown that magnetism has a significant influence upon the human body. Existing magnetic therapy devices have been developed and documented to reduce inflammation in tissues and for pain relief. Magnetic fields are known to improve blood flow to the tissues when applied. It has also been shown that a rapid rate of magnetic field change provides enhanced effect over fixed magnetic field therapy; see for example U.S. Pat. Nos. 5,529,568, 5,667,469, 6,102,875 and 6,231,947.

In U.S. Pat. No. 5,529,568 a magnetic operating table is disclosed having a magnetic pull above and below the table with the pull above the table controlling the selective focus of the magnetic fields.

U.S. Pat. No. 5,667,469 discloses a strong magnetic therapy apparatus that uses permanent magnets positioned on a rotating device. The pole magnets are in spaced relation to one another and are arranged annularly about the rotating surface.

U.S. Pat. No. 6,102,875 claims an apparatus for combined application of physical massage, acupressure and a biomagnetic therapy. A plurality of massage balls are mounted on a rotor with multiple magnets positioned below a drive motor and the rotor.

U.S. Pat. No. 6,231,497 discloses a magnetic therapy device having permanent magnets that are rotated in the primary form of the invention and oscillated in an alternate form. Magnets are rotated about a drive shaft or placed on the end of a rotating shaft when the magnetic poles so formed extend outwardly in a trans-angular inclination to the magnetic rotation vortex.

Applicant's device provides for a linearly aligned alternating polar magnetic fields rotating about their polar and longitudinal axis in spaced relation to a corresponding polar arranged fixed linear aligned magnetic field element.

SUMMARY OF THE INVENTION

The present invention is directed to an apparatus that provides therapeutic treatment by using dynamic magnetic fields. Two sets of magnets are used to create a magnetic field compression therebetween wherein a first set of magnets are rapidly rotated in relation to a fixed set. The rate of magnetic field change induced by the linear aligned opposing pole magnets rotated on their longitudinal axis is in variable opposition to magnetic fields of the opposing set of fixed polar aligned magnets in vertical spaced aligned relation thereto.

DESCRIPTION OF THE PREFERRED EMBODIMENT

Figure 1:
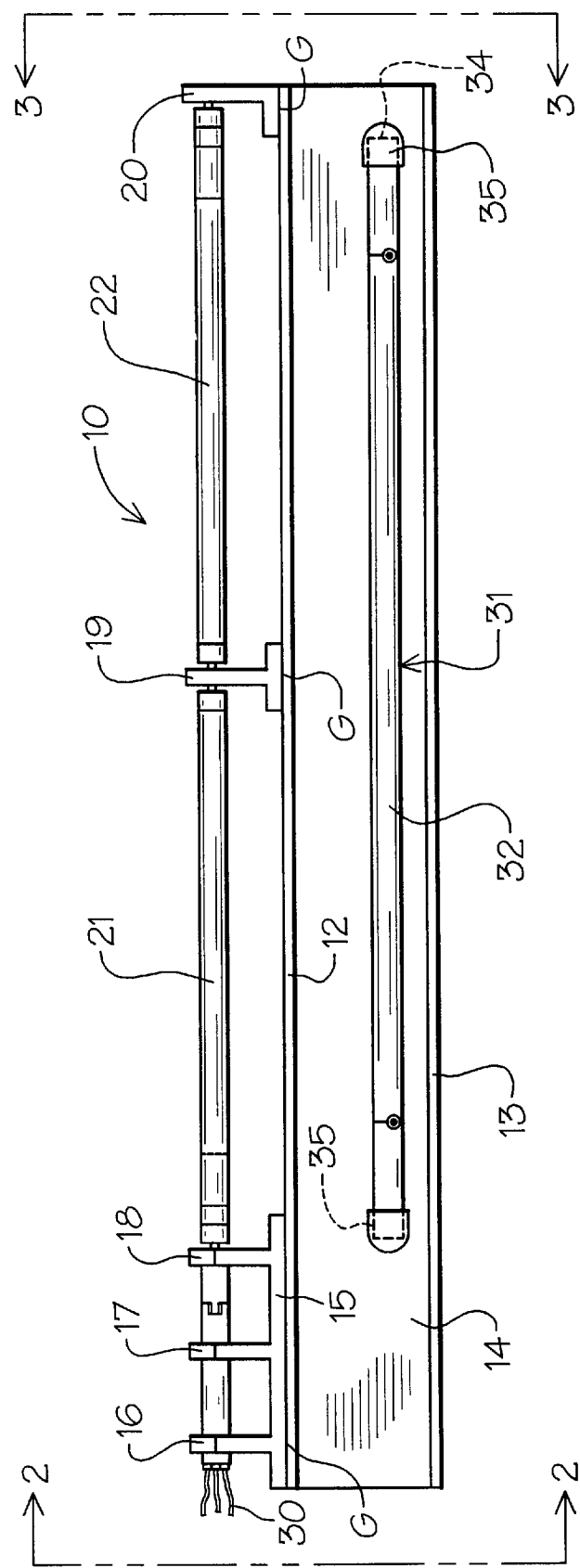
FIG. 1 is a side elevational view of the therapeutic device.
Figure 2:
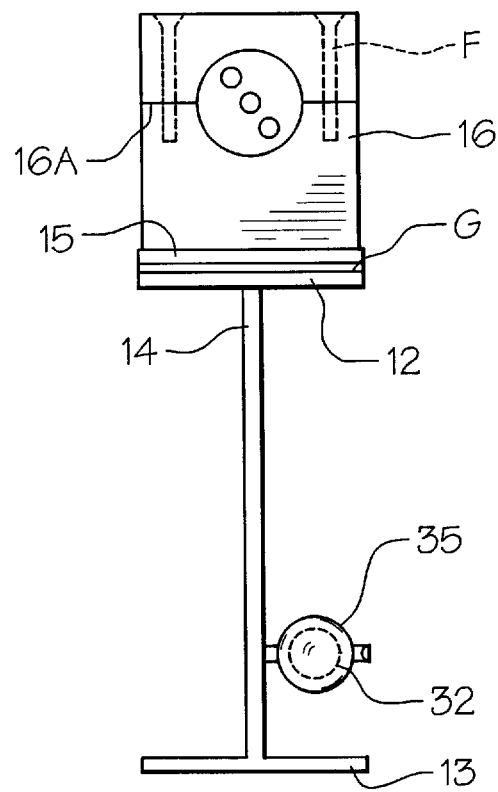
FIG. 2 is an enlarged end plan view on lines 2—2 of FIG. 1.
Figure 3:
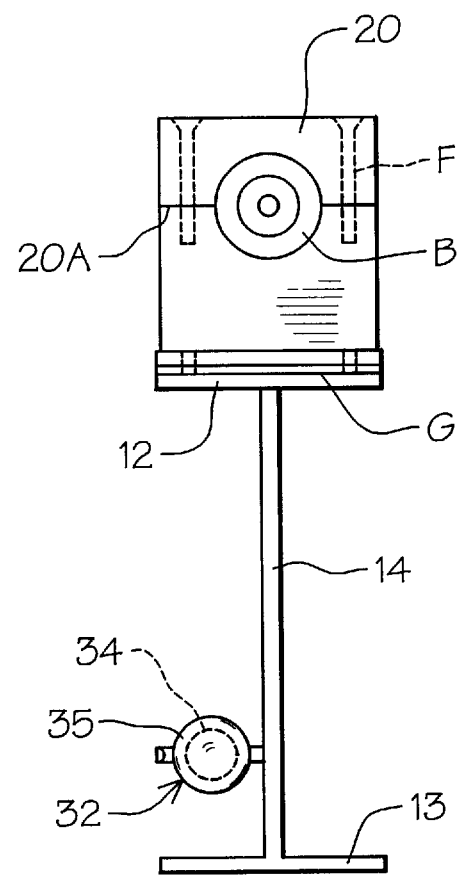
FIG. 3 is an enlarged end plan view on lines 3—3 of FIG. 1.

Referring to FIG. 1 of the drawings, the magnetic therapeutic device 10 of the invention can be seen having an elongated support mounting base 11 with an integral mounting platform 12 and ground engagement base 13. A support web 14 interconnects the respective mounting platform 12 and base 13 defining an I-beam configuration in cross-section. A primary mounting bracket 15 is secured to the mounting platform 12 with an insulating gasket G positioned therebetween by fasteners F and can be seen to have a plurality of upstanding mounting brackets 16, 17 and 18 extending therefrom. The mounting brackets 16, 17 and 18 are apertured at 16A, 17A and 18A respectively and are horizontally split therethrough and are secured together by multiple fasteners F as will be evident to one skilled in the art. A mid support bracket 19 is positioned in spaced longitudinal relation to the primary mounting bracket 15 and an end supporting bracket 20 in spaced longitudinal relation thereto. Both the mid and end supporting brackets 19 and 20 are apertured and split as hereinbefore described and are secured to the mounting platform 12.

The mounting brackets 18, 19 and 20 accordingly define high speed bearing mounts as will be described in greater detail hereinafter.

Figure 4:
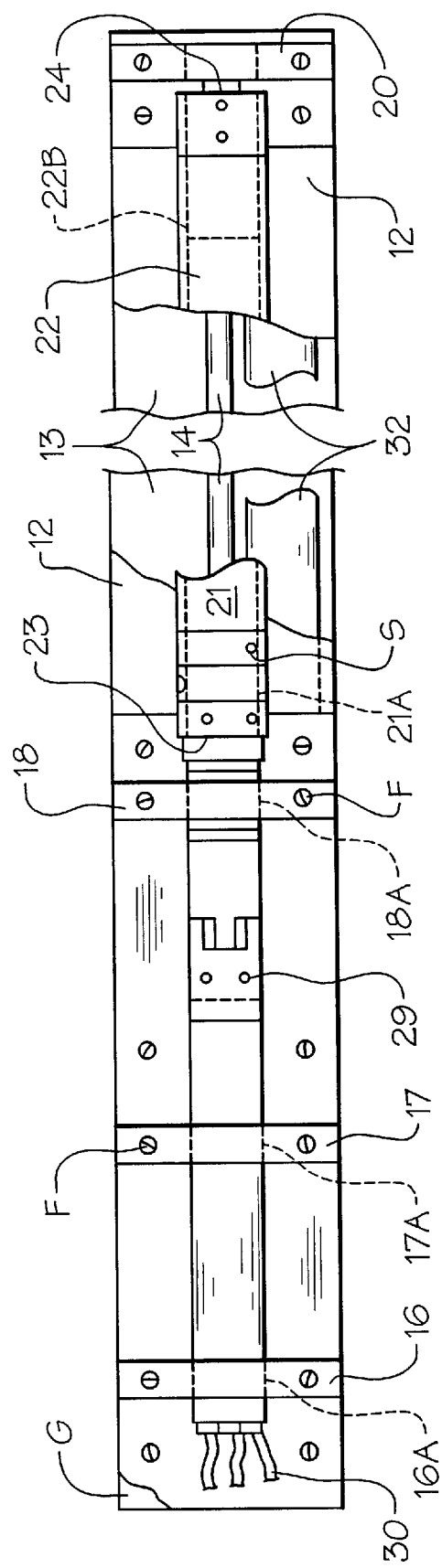
FIG. 4 is an enlarged top plan view of a drive portion of the therapeutic device.
Figure 5:
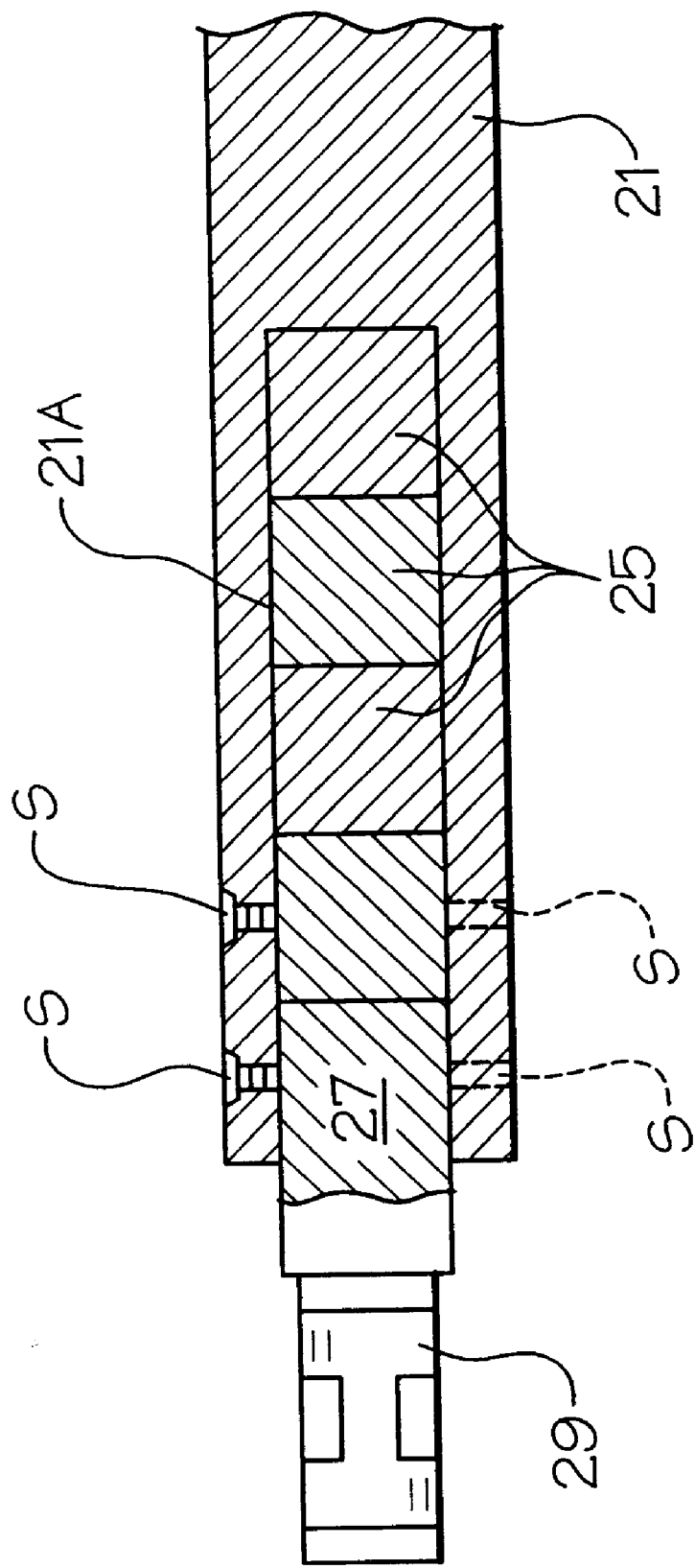
FIG. 5 is an enlarged partial cross-sectional view of the magnetic bar assembly of the therapeutic device.

A pair of drive magnet bars 21 and 22 are positioned between the respective high speed bearing mount brackets 18, 19 and 20 respectively as best seen in FIG. 1 of the drawings. Each of the drive magnetic bars 21 and 22 is ported inwardly at 21A and 22B on their oppositely disposed respective ends 23 and 24 for registration within of selected groupings of rare earth pole magnets 25 as illustrated in FIGS. 4 and 5 of the drawings. The pole magnets 25 are typically of an annular disk configuration having a north and south pole. The magnets 25 are of different static magnetic strengths in the range of 50 gauze to 100,000 gauze and can be selected in varying combinations for registration within the drive magnetic bars 21 and 22 and held within the respected ported ends 21A and 22B by multiple set screws S threadably engaged through correspondingly aligned apertures in outer cylindrical wall 26.

Bearing journal inserts 27 are secured with the respective ported opening 21 by a second set of multiple setscrews S, as noted above.

A pneumatic motor 28 is inner-engaged on the corresponding journal end at 29 of the drive magnetic bar 21 and registerably engaged within the respective mounting brackets 16 and 17. The pneumatic motor 28 is connected to a source of fluid under pressure, not shown, by supply and return lines 30 as illustrated in FIGS. 1 and 4 of the drawings.

A static magnet mount 31 can be seen in FIGS. 1, 2, 3 and 7 of the drawings having a cylindrical body member 32 that is affixed to the support web 14 of the mounting base 11 in vertical spaced aligned relation to the rotating magnetic bars 21 and 22. The cylindrical body member 32 also has a plurality of selected polar magnets 25 of varying strengths positioned in each end at 33 and 34. End retaining caps 35 secure the selected magnets 25 as hereinbefore described there within.

Figure 6:
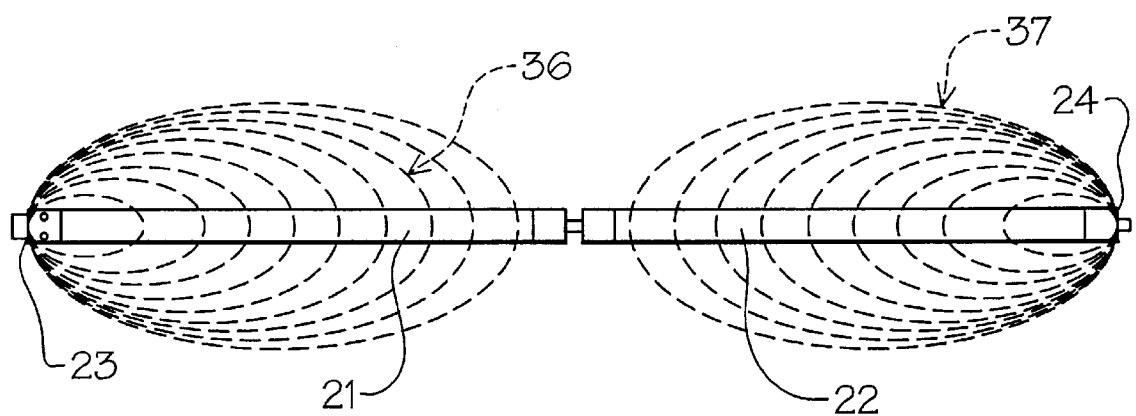
FIG. 6 is a graphic illustration of the primary magnetic fields of the rotation bar.
Figure 7:
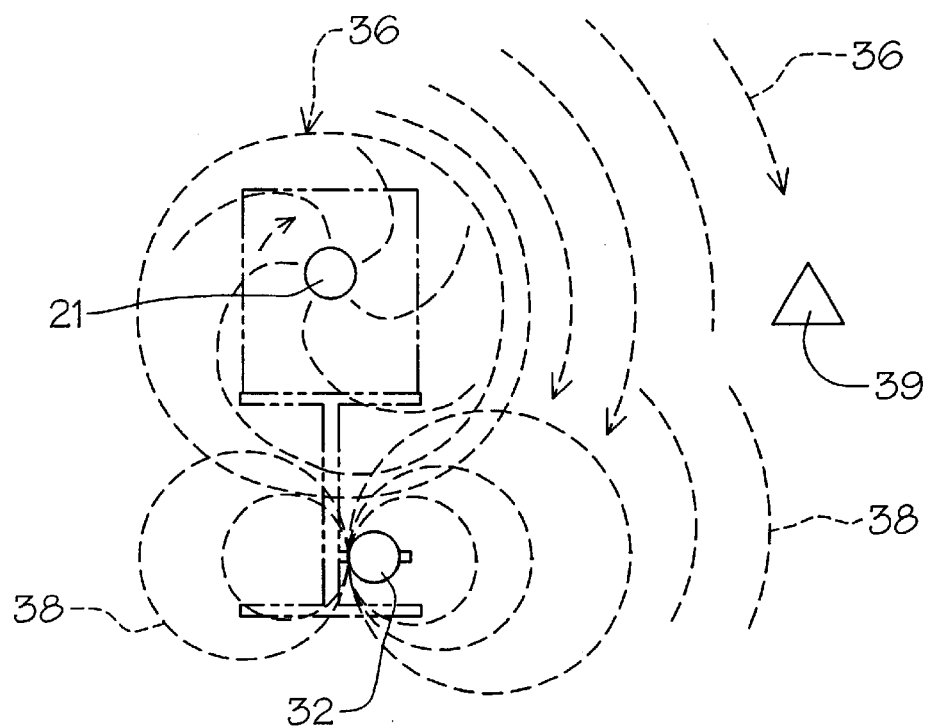
FIG. 7 is a graphic end view of the primary magnetic fields in motion and fixed magnetic fields.

Referring now to FIGS. 6 and 7 of the drawings, magnetic fields 36 and 37 are graphically illustrated for both of the rotating magnetic bars 21 and 22. In FIG. 7 of the drawings, the rotation of the magnetic bars 21 and 22 at high speed is illustrated for disclosure purposes only and not as an actual magnetic field so generated by high speed rotation which would be difficult to actually illustrate.

Magnetic polar north and south flux spring defines a multiple magnetic field of halfway formed therefrom. This high-speed rotation of the magnetic bars 21 and 22 in relation to a magnetic field 38 generated from the static magnetic mount 31 imparts a so-called compression of the respective magnetic fields that will emanate outwardly to induce a therapeutic effect generally illustrated at 39.

It will be evident from the above description that the various mounting components of the therapeutic device 10 of the invention must be of non-ferrous material so that they will not interfere with the magnetic fields generated during use. It will also be seen that the high-speed rotation of the linearly disposed polar magnet assemblies in longitudinally spaced relation to one another imparts the therapeutic effectiveness so defined to a compressed magnetic waveform of increasing therapeutic action.

It will thus be seen that a new and useful magnetic therapy device has been illustrated and described and that various changes and modifications may be made thereto without departing from the spirit of the invention.

Therefore I claim:

1. A magnetic therapy device comprising, a first set of multiple permanent polar magnets in spaced longitudinal polar aligned relation to one another, a second set of multiple permanent polar magnets in spaced longitudinal polar aligned relation, one of said first set of permanent polar magnets rotating on its longitudinal axis, said first and second set of permanent polar magnets in spaced vertical relation to one another, said magnetic sets mounted on a non-ferrous mounting base, dive means for rotating said magnetic sets and means for rotatably securing said magnet sets on a non-ferrous mounting base.

2. The magnetic therapy device set forth in claim 1 wherein said first magnetic set comprises, a mounting bar, magnet receiving recesses formed inwardly from its respective ends and means for securing said magnets within said magnet receiving recesses.

3. The magnetic therapy device set forth in claim 1 wherein said sets of multiple permanent polar magnets are comprised of individual rare earth polar magnets having independent magnetic values.

4. The magnetic therapy device set forth in claim 1 wherein said second magnetic set comprises an elongated cylinder secured to said mounting base.

5. The magnetic therapy device set forth in claim 1 wherein said means for rotatably securing said rotatable magnet set comprises a plurality of upstanding journal bearing brackets adjacent respective ends of said magnetic sets.

6. The magnetic therapy device set forth in claim 1 wherein said drive means for rotating said rotatably magnet sets comprises, a high-speed pneumatic motor.

7. The magnetic therapy device set forth in claim 4 wherein said second magnetic set elongated cylinder has a plurality of multiple strength permanent magnets in selected groups in oppositely disposed relation to one another and means for securing said magnetic sets within said elongated cylinder.

8. The magnetic therapy device set forth in claim 7 wherein said means for securing said multiple magnetic sets within said elongated cylinder comprises independent end caps on said cylinder and fasteners extending through said cylinder in spaced relation to respective end caps.

* * * * *